United States Patent [19]

Labeeuw et al.

[11] Patent Number: 4,593,022

[45] Date of Patent: Jun. 3, 1986

[54] DERIVATIVES OF PYRIDINIUM THIOMETHYL CEPHALOSPORINS

[75] Inventors: Bernard Labeeuw, Montpellier; Ali Salhi, Saint-Gely-du-Fest, both of France

[73] Assignee: Sanofi, Paris, France

[21] Appl. No.: 441,757

[22] Filed: Nov. 15, 1982

[30] Foreign Application Priority Data

Nov. 16, 1981 [FR] France ............... 81 21385

[51] Int. Cl.[4] .................. C07D 501/38; A61K 31/545
[52] U.S. Cl. ..................... 514/206; 544/25; 544/27
[58] Field of Search ............... 544/25, 26, 27; 424/246; 514/206

[56] References Cited

U.S. PATENT DOCUMENTS 4,237,128 12/1980 Cimarusti et al. ............ 544/25
4,315,005  2/1982 Ayrs et al. .................. 544/25

FOREIGN PATENT DOCUMENTS 2027691  2/1980  United Kingdom .
2036738  7/1980  United Kingdom .
2046261 11/1980  United Kingdom .
1603712 11/1981  United Kingdom .
1604723 12/1981  United Kingdom .
1604724 12/1981  United Kingdom .

Primary Examiner—Nicholas S. Rizzo

Attorney, Agent, or Firm—Weingarten, Schurgin, Gagnebin & Hayes

[57] ABSTRACT

The present invention relates to cephalosporins of general formula:

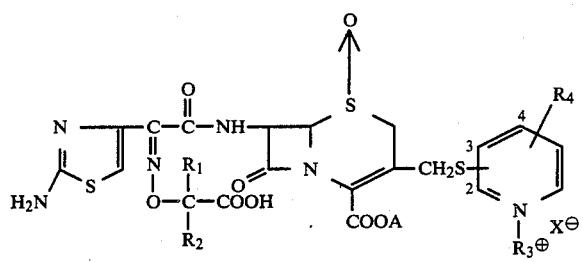

in which:

$R_1$ is H or $CH_3$, $R_2$ is $CH_3$, or $R_1$ and $R_2$ taken together form a 1,3-propylene group, $R_3$ is lower alkyl, alkenyl, alkynyl or $CH_2COO$ alkyl, $R_4$ is H or OH, the S being bonded to the pyridine ring in 2 or 4 position, A is H or cation or ester or hemiacetal which is easily hydrolyzable, and X is a derivative of a mineral or organic acid.

The invention also relates to a process for preparing these new cephalosporins and to the drugs containing said cephalosporins.

11 Claims, No Drawings

DERIVATIVES OF PYRIDINIUM THIOMETHYL CEPHALOSPORINS

The present invention relates to new derivatives of cephalosporins, to a process for preparing them and to pharmaceutical compositions containing said derivatives of cephalosporin as active ingredients.

More particularly, the present invention relates to new cephalosporins substituted in 3 position by a pyridinium thiomethyl group.

Belgian Pat. No. 866 038 describes a series of sulfoxides and sulfones of cephalosporins of general formula:

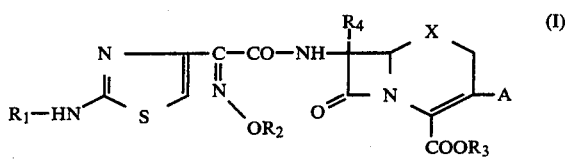

in which X=SO, $SO_2$.

Among the radicals indicated for A, this Patent mentions in particular $CH_2SR_5$ groups where $R_5$ may be possibly substituted pyridyl.

The cephalosporins of formula (I) are generally supposed to possess a very strong bacterial activity against gram positive and gram negative bacteria and to be highly effective against the penicillinase-producing staphylococci.

Furthermore, West German patent application No. 2 921 332 describes a family of cephalosporins of general formula:

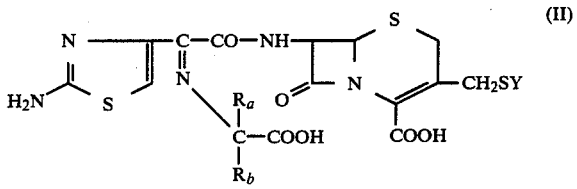

in which Y may in particular be

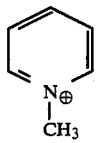

These cephalosporins are presented as broad-spectrum antibiotics.

It is an object of the present invention to produce new cephalosporins which have a bacterial profile very different from that of the compounds of the Patents mentioned hereinabove. In fact, the compounds of the invention have remarkable activity on enterobacteria, including those producing β-lactamases, good activity on Pseudomonas and weak activity on staphylococci.

These new cephalosporins correspond to general formula:

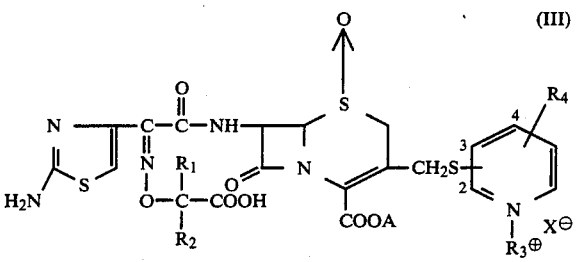

in which:

$R_1$ represents hydrogen or a methyl group, $R_2$ represents a methyl group, or $R_1$ and $R_2$ taken together represent a 1,3-propylene group;

$R_3$ represents a lower alkyl group, a lower alkenyl group or a lower alkynyl group or a $CH_2COO$ Alk group (Alk representing a lower alkyl group), $R_4$ denotes H or OH occupying a free position of the pyridine ring, the atom of sulfur of the thiomethyl group being bonded in 2 or 4 position of the pyridine ring, A represents hydrogen, a cation or an ester or hemiacetal which is easily hydrolysable or metabolically labile and pharmaceutically acceptable, and $X^\ominus$ represents an anion derived from a pharmaceutically acceptable mineral or organic acid such as chloride, bromide, acetate, trifluoroacetate, formate ..., Under certain conditions, it is also possible to salify the pyridinium by the carboxylateanion carried by the cepheme ring. In this case, $X^\ominus$ is the carboxylateion. These "inner salts" form an integral part of the invention.

In the present application:

The term "lower alkyl" denotes the radical of a saturated aliphatic hydrocarbon containing up to 4 atoms of carbon.

The term "lower alkenyl" denotes the radical of an aliphatic hydrocarbon presenting a double bond and containing up to 4 atoms of carbon.

The term "lower alkynyl" denotes the radical of an aliphatic hydrocarbon presenting a triple bond and containing up to 4 atoms of carbon.

The term "cation" denotes an alkaline or alkaline-earth ion, preferably the sodium, potassium or calcium ions or the "ammonium" derivative resulting by protonation of a pharmaceutically acceptable organic amine such as ethylene-diamine, ethanolamine, tromethamine and the like to form addition salts.

The term ester or hemiacetal which is easily hydrolyzable or metabolically labile and pharmaceutically acceptable denotes radicals such as phthalidyl, pivaloyloxymethyl, acetoxymethyl, ethoxycarbonyloxymethyl, 1-(ethoxycarbonyloxy)ethyl, acetonyl, α-methoxy α-carbomethoxymethyl, carbomethoxymethyl, carbethoxymethyl and the like.

The invention relates in particular to the compounds of formula III which are selected from:

a pharmaceutically acceptable mineral or organic quaternay salt of the syn isomer of 7-[2-(2-amino 4-thiazolyl)2-(2-carboxy 2-propyl oxyimino)acetamido]3-(N-allyl 2-pyridinio thiomethyl)3-cepheme 4-carboxylic S-oxide-1 acid of formula:

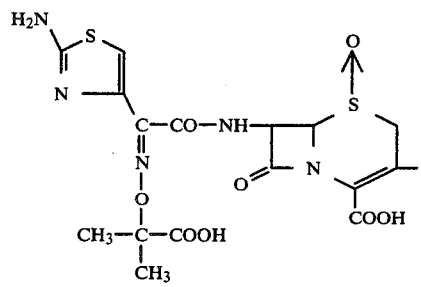
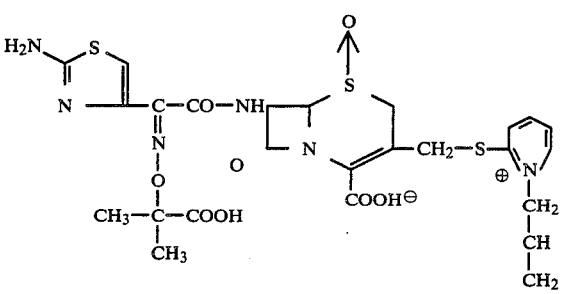

and the products obtained by salification, esterification or hemiacetalization of at least one carboxylic function of said salt and possible salification of the amine function of said salt.

and the inner quaternary salt of the syn isomer of the abovementioned acid, said product having as formula:

and the products obtained by salification or esterification or hemiacetalization of the acid function of said inner salt and possible salification of the amine function of said salt.

The invention relates more particularly to the trifluoroacetate of the syn isomer of 7-[2(2-amino 4-thiazolyl)2-(2-carboxy 2-propyl oxyimino)acetamido]3-(N-allyl 2-pyridinio thiomethyl)3-cepheme 4-carboxylic S-oxide-1 acid, or the bromide of the hydrochloride of said acid or the chloride of the hydrochloride of said acid.

The invention also relates to a process for preparing the compounds of formula (III)

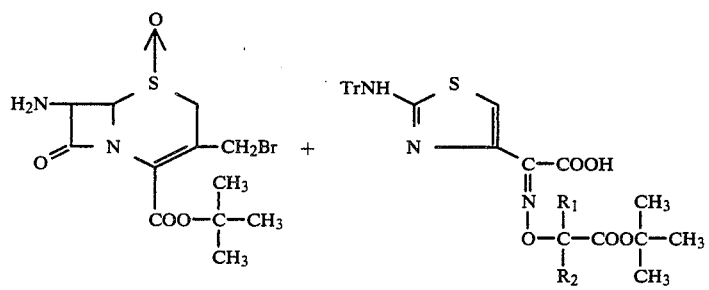

(IV)    (V) Tr = Trityl

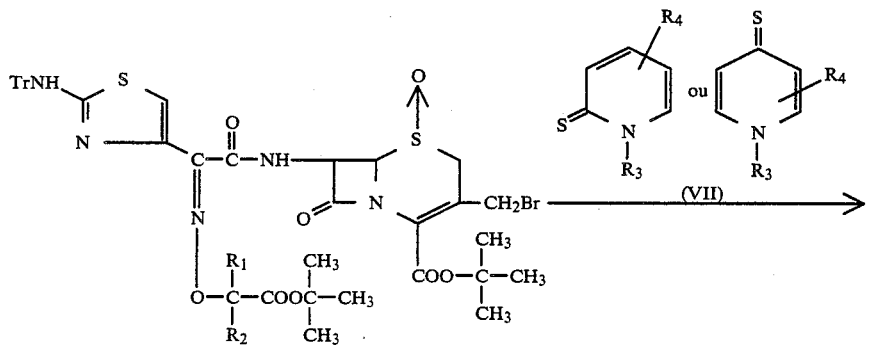

(VI)

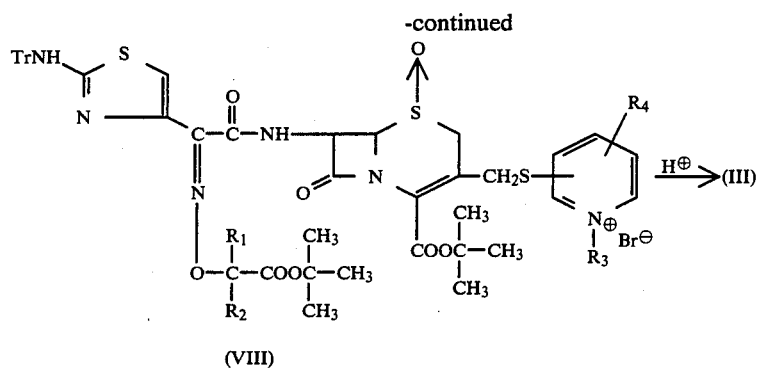

(VIII)

The first step consists in acylating the 7-amino 3-bromomethyl 3-cepheme carboxylate of tertiobutyl S-oxide-1 (IV) by the acid (V). Before effecting the reaction of acylation, it is desirable to protect the amino group of the acid (V) by a protector group easy to eliminate subsequently. The groups usually used in organic synthesis may be used for the protection of the amines and, in particular, the trityl group. to effect the reaction of acylation, it is necessary to proceed with activation of the carboxyl group of compound (V), preferably by transformation into anhydride with the aid of a carbodiimide, generally dicyclohexylcarbodiimide.

The reaction of activation is effected within a suitable organic solvent such as tetrahydrofuran at a temperature of between 0° and 50° C. and preferably at ambient temperature. The reaction of activation is possibly facilitated by addition of a hydroxylated derivative such as 1-hydroxy benzotriazole.

The solution of the reagent of acylation thus obtained, from which the dicyclohexylurea formed is removed by filtration, is added to a solution of compound (IV) in an aprotic polar solvent such as dimethylformamide. The addition of the two reagents may also be effected in the reverse order.

By action on the compound (VI) thus obtained of a pyridine 2-thione or of a pyridine 4-thione (VII) carrying on the nitrogen the substituent $R_3$ and possibly substituted on the ring by $R_4$, compound (VIII) is obtained in the form of bromide of quaternary ammonium.

The reaction is carried out within a suitable aprotic polar solvent such as dimethylformamide or N,N-dimethylacetamide at a temperature of between 0° and 50° C. and preferably at ambient temperature.

The product (VIII) is isolated by precipitation by addition of a solvent where it is slightly soluble, such as isopropyl ether, then purified by the conventional methods and, in particular, by chromatography over silica gel.

The series of operations which allow passage from the brominated derivative (IV) to compound (VIII) may also be carried out in the reverse order: substitution of the brominated derivative (IV) by the thione (VII) followed by acylation on nitrogen by the acid (V).

Finally, to arrive at compounds (III), the protector groups on the amine of the carboxyl functions are simultaneously eliminated by a known process, in particular by hydrolysis in acid medium by using an organic acid such as formic acid or trifluoroacetic acid.

As far as the raw materials used in this process are concerned, compounds (IV) and compounds (V) as well as their derivatives in which the amino group is blocked by a protector group, are known.

The pyridine thiones (VII) may be prepared from the corresponding bromopyridines according to the scheme:

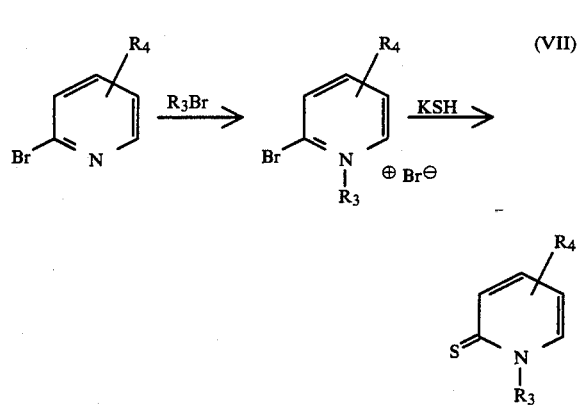

This scheme shown here for obtaining the pyridine 2-thiones is also applied to the preparation of the pyridine 4-thiones from the 4-bromo pyridines.

The first step consists in quaternizing a possibly substituted bromopyridine by action of the bromide $R_3Br$. Operation consists most often of heating the reagents to reflux.

On the quaternary derivative thus obtained, the action of potassium hydrosulfide in aqueous solution leads to the pyridine thione (VII).

Compounds (III) according to the invention may also be prepared from the 7-formylamino cephalosphoranic acid according to the following reaction scheme:

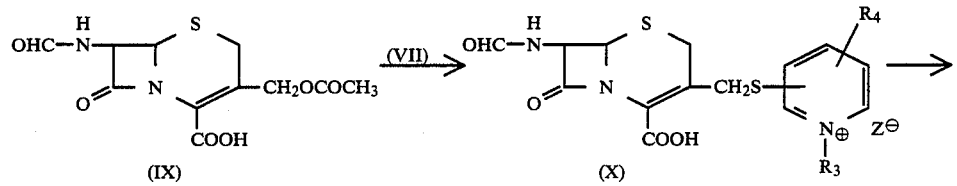

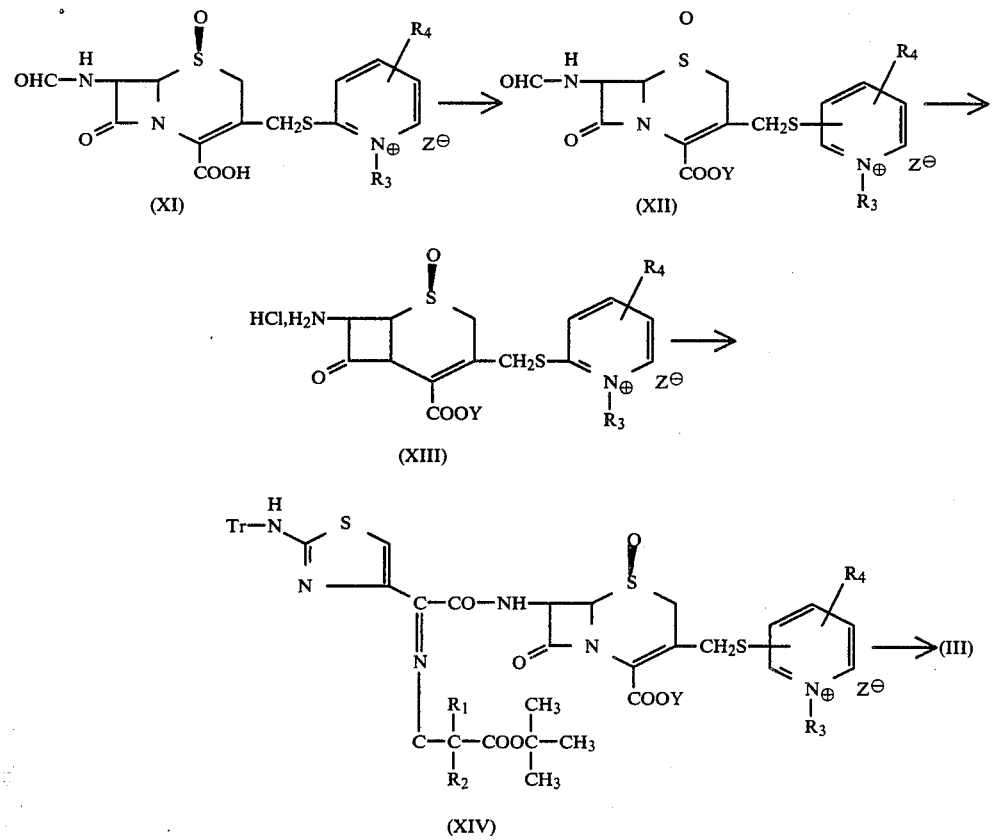

Tr = trityl
Z = mineral anion

The first step consists in causing a pyridine thione (VII) to act on the 7-formylamino cephalosporanic acid (IX) or preferably an alkaline salt thereof. Operation is then carried out in aqueous solution in the presence of sodium iodide at a temperature of between 40° and 80° C. The product (X) is then isolated in the form of pyridinium iodide and possibly of alkaline salt.

For the following step, the carboxylic acid function is released by action of an acid such as hydrochloric acid then, preferably, for reasons of stability, the pyridinium iodide is converted into chloride by passage over an ion exchanger column in the form of hydrochloride.

The product (X) is then converted into corresponding sulfoxide (XI) by action of hydrogen peroxide or of a peracid such as metachloroperbenzoic acid. The sulfoxide (XI) is then converted into ester (XII) in which the group Y represents a group which will subsequently be easy to eliminate such as the diphenylmethyl, tertiobutyl or trimethylsilyl group.

The compound (XII) is deformylated on amino nitrogen, for example by action of the thionyl chloride within the methanol. The 7-amino compound is isolated in the form of hydrochloride (XIII). The latter is acylated on nitrogen, using the chloride of the acid:

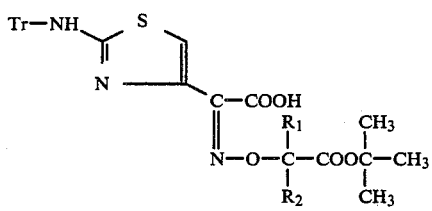

Tr = trityl

The reaction of acylation is effected in a solvent such as methylene chloride in the presence of dimethylaniline. In this way is obtained the protected cephalosporin (XIV) which, by treatment in strong acid medium, leads to the compounds (III) according to the invention. In particular, the hydrochloric acid-formic acid mixture may be used for effecting deprotection, or trifluoroacetic acid.

Compounds (III) may also be prepared from the Cephalosporin C according to the following reaction diagram:

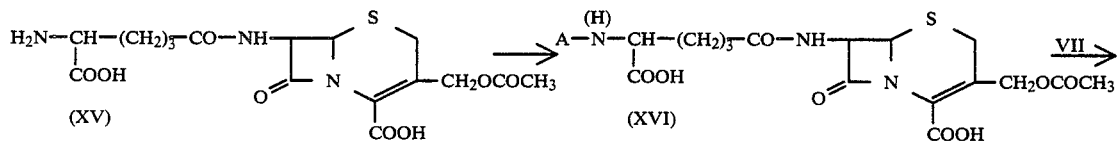

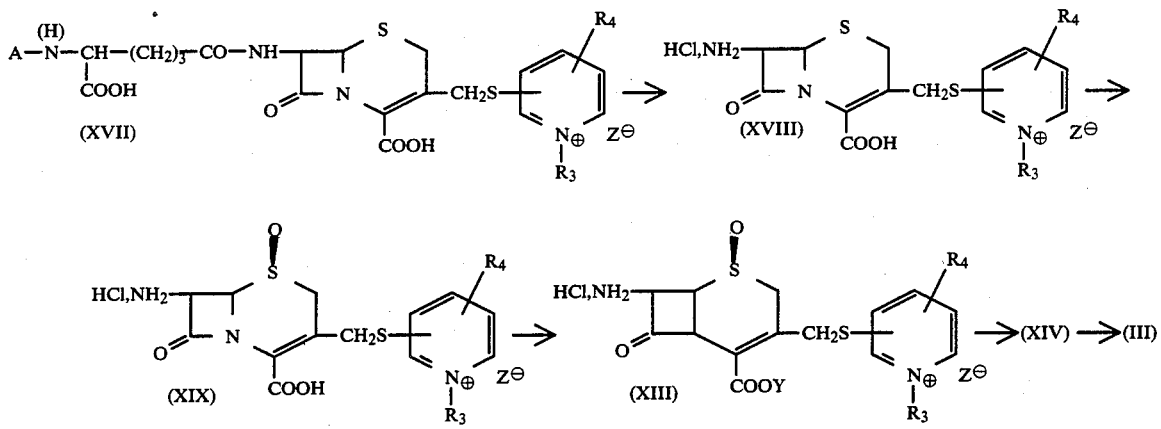

The first step consists in blocking the primary amine function of the cephalosporin C by a protector group A, according to a known process.

Among the protector groups which may be used, mention may be made of the phthalidyl group or ethoxycarbonyl group. From compound (XVI), the quaternary ammonium compound (XVII) is obtained by action of a pyridine thione (VII). Operation is carried out in aqueous solution in the presence of sodium iodide and sodium bicarbonate intended to salify the carboxyl functions of the starting product.

The acyl chain is then cut from compound (XVII). After having blocked the carboxylic functions of compound (XVII), for example by formation of trimethylsilyl ester), the cut of the acyl chain is effected by action of phosphorus pentachloride of an alcohol such as methanol or a diol such as 2,3-butanediol. In this way the compound (XVIII) is isolated in the form of hydrochloride of the primary amine and of pyridinium chloride ($Z^- = Cl^-$).

Compound (XVIII) is converted into corresponding sulfoxide derivative (XIX) by action of an organic peracid such as metachloroperbenzoic acid in acid medium.

The acid (XIX) is esterified by a labile group such as the diphenylmethyl or tertiobutyl group to lead to the ester (XIII) or protected by a trimethylsilyl group.

From compound (XIII), compounds (III) are arrived at in 2 steps as indicated hereinabove.

Compounds XIII, XIII, XIX and XX are new and constitute the key intermediaries of the process of the present invention. They may be grouped in the following general formula

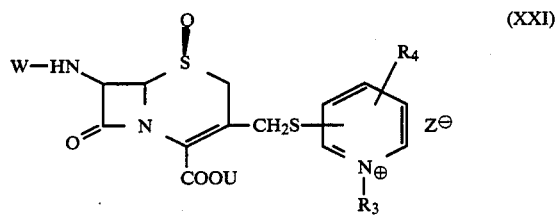

where $R_3$, $R_4$ and Z are such as defined hereinabove, U represents hydrogen or a group easy to eliminate by hydrolysis or hydrogenolysis and W represents hydrogen or a formyl group. Compounds XXI hereinabove as well as their acid addition or possible mineral salts represent a subsequent aspect of the present invention.

The compounds of formula XXI where U, $R_4$ and W are hydrogen, $R_3$ is allyl and Z is chlorine, and its hydrochloride as well as compound XXI where U and $R_4$ are hydrogen, W is formyl, $R_3$ is allyl and Z is chlorine, are the preferred intermediate compounds.

The compounds (III) of the invention, in which A is other than H, are obtained from the compounds (III) in which A is H by reactions known per se.

In this way, the mineral salts are obtained by action on compounds (III) in which A=H of a mineral base such as sodium or potassium hydroxide or sodium bicarbonate, in equimolecular quantity. Reaction is effected in a solvent such as water or ethanol and the salt obtained is isolated by evaporation of the solution. The salts of organic bases are obtained by action, on a solution of the acid (III A=H) in a solvent or a mixture of suitable solvents, of an equimolecular quantity of the organic base. The salt is isolated by precipitation with ether.

The esters are obtained by the known processes of esterifiction; for example, the action of a halogen derivative on a salt such as the sodium salt of the acid will advantageously be used. Reaction will preferably be carried out in a solvent capable of dissolving the starting acid derivative, for example in dimethylformamide.

The isomers of syn and anti form are obtained by suitably selecting the reagents.

The following examples will enable the scope of the invention to be more readily understood.

As is usual in this family of compounds, the products according to the invention do not present a clear melting point, but only points of decomposition which do not enable them to be characterized.

The products will therefore be characterized by their nuclear magnetic resonance spectrum recorded at 60 MHz, the inner standard being hexamethyldisiloxan.

The following abbreviations will be used:
S: singlet
D: doublet
T: triplet
Q: quadruplet
D of D: doublet of doublet
S.e.: enlarged singlet
M: multiplet
AB: system AB
J: represents the coupling constant.

Moreover, elementary microanalyses have been made in each case and are in agreement with the formulae indicated.

EXAMPLE 1

Trifluoroacetate of 7-[2-(2-amino 4-thiazolyl)2-(2-carboxy 2-propyl oxyimino)acetamido]3-(N-allyl 2-pyridinio thiomethyl)3-cepheme 4-carboxylic S-oxide-1 acid, syn isomer (CM 40 874)

(III) $R_1=R_2=CH_3$; $R_3=-CH_2CH=CH_2$; $R_4=H$; $A=H$; $X=CF_3COO^-$ (a) N-allylpyridine 2-thione The mixture of 5 g of 2-bromo pyridine and 4.2 g of allyl bromide is heated to 70° C. for 2 hrs. 30 mins. 10 ml of acetone are added and the crystals of N-allyl 2-bromo pyridinium bromide are drained and washed with acetone then with ether and dried.

A solution of potassium hydrosulfide is prepared by bubbling a stream of sulfuretted hydrogen in a solution of 2.6 g of potassium hydroxide in 40 ml of water up to decoloration of the phenolphthaleine. 2 g of the product obtained hereinabove are then added and the mixture is stirred at 20° C. for 15 mins., and extracted three times with 50 ml of methylene chloride. The solution is dried over magnesium sulfate and the solvent is evaporated to dryness.

1 g of N-allylpyridine 2-thione is thus obtained in the form of a yellow oil.

(b) 7-[2-(2-tritylamino 4-thiazolyl)2-(2-t-butoxycarbonyl 2-propyl oxyimino)acetamido]3-bromomethyl 3-cepheme carboxylate of 4-tertiobutyl S-oxide 1, syn isomer (VI) $R_1=R_2=CH_3$ To a solution of 5 g of hydrochloride of 7-amino 3-bromomethyl 3-cepheme carboxylate of 4-tertiobutyl S-oxide-1 in 90 ml of methylene chloride are added 1.72 ml of triethylamine, 7.57 g of 2-(2-tritylamino 4-thiazolyl) 2-(2-t-butoxycarbonyl 2-propyl oxyimino)acetic acid, 2.84 g of dicyclohexylcarbodiimide and 0.1 g of hydroxybenzotriazole. The mixture is stirred for 15 hours at ambient temperature, then the dicyclohexylurea formed is filtered.

After evaporation of the solvent, the residue is chromatographed over a silica gel column (250 g). By eluting with a hexane-ethyl acetate 50-50 (vol/vol) mixture, 4.3 g of the expected product are obtained.

NMR spectrum (in solution in deuterium dimethylsulfoxide): 1H at 8.70 ppm (NH-Trit, S)-1H at 8.07 ppm (NH—CO, D, J=9 Hz)-15H at 7.25 ppm (H Trit, S)-1H at 6.72 ppm (H thiazole, S)-1H at 5.88 ppm(H$_7$, D of D, J$_1$=9 Hz, J$_2$=4 Hz)-1H at 4.96 ppm (H$_6$, D, J=4 Hz)-2H at 4.50 ppm(CH$_2$Br, AB, J$_{AB}$=12 Hz)-2H at 3.77 ppm (CH$_2$ in 2, S.e. 9H at 1.45 ppm

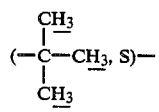

6H at 1.37 ppm

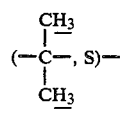

9H at 1.27 ppm

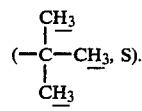

(c) Bromide of 7-[2-(2-tritylamino 4-thiazolyl)2-(2-t-butoxycarbonyl 2-propyl oxyimino)acetamido]3-(N-allyl 2-pyridinio thiomethyl)3-cepheme carboxylate of 4-t-butyl S-oxide-1, syn isomer (VIII) $R_1=R_2=CH_3$; $R_3=CH_2—CH=CH_2$; $R_4=H$ The mixture of 0.7 g of the brominated derivative obtained in the preceding paragraph and 0.14 g of N-allyl-pyridine 2-thione in 4 ml of N,N-dimethylacetamide is left for 3 hours at 20° C. The mixture is precipitated by addition of isopropyl ether and the solid is drained and washed with isopropyl ether. The solid is dissolved in the minimum of methylene chloride and chromatographed over a column of 20 g of silica gel.

By eluting with the methylene chloride-methanol 90-10 (vol/vol) mixture, 0.65 g of the expected product is obtained.

(d) CM 40 874

The solution of 0.57 g of the protected product obtained hereinabove in 6 ml of trifluoroacetic acid is left for 45 mins. at 20° C. It is concentrated in vacuo to about 3 ml then precipitated by addition of ether. The solid is drained and dried.

0.39 g of the expected product is thus obtained.

NMR spectrum: 1H at 9.05 ppl (H$_6$, pyridine, D, J=5 Hz)-1H at 8.50 ppm (NHCO, D, J=9 Hz)-1H at 8.35 ppm (H$_4$, pyridine, M)-1H at 8.20 ppm (H$_3$, pyridine, D, J=7 Hz)-1H at 7.95 ppl (H$_5$, pyridine, M)-4H between 7 and 10 ppm (2 COOH, NH$_2$)-1H at 6.82 ppm (H thiazole, S)-2H at 6.0 ppm (H$_7$ and CH=, M)-5H between 5.0 and 5.6 ppm (CH$_2$N$^+$, CH$_2$= and H$_6$, M)-1H at 4.5 ppm (CH$_2$S, A of AB, J$_{AB}$=13 Hz)-1H at 4.32 ppm (CH$_2$S, B of AB, J$_{AB}$=13 Hz)-1H at 4.0 ppm (CH$_2$S→O, A of AB, J$_{AB}$=17 Hz)-1H at 3.8 ppm (CH$_2$S→O, B of AB, J$_{AB}$=17 Hz)-6H at 1.45 ppm

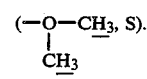

EXAMPLE 2

Hydrochloride, bromide of 7-[2-(2-amino 4-thiazolyl) 2-(2-carboxy 2-propyl oxyimino)acetamido]3-(N-allyl 2-pyridinio thiomethyl)3-cepheme 4-carboxylic S-oxide-1 acid, syn isomer (CM 40 874 b)

9.3 g of the protected compound obtained in Example 1 (c) are dissolved in 55 ml of 99% formic acid then 3.3 ml of concentrated hydrochloric acid are added drop by drop and the mixture is left for 1 hour with stirring at 25° C. The solid formed is filtered and washed with 25 ml of 50% formic acid. The filtrate is evaporated to dryness in vacuo at ambient temperature. The residue is redissolved in 100 ml of absolute ethanol and again evaporated to dryness in vacuo at ambient temperature. The residue is again dissolved in 50 ml of methanol and the solution is poured, with stirring, in 300 ml of ether. The precipitate is drained and washed with ether.

6.5 g of the expected product are thus obtained, which is purified by dissolution in 50 ml of methanol, the solution being poured slowly with stirring in 300 ml of ether.

After draining and drying, 6.2 g of CM 40 874 b are finally obtained.

NMR spectrum: 1H at 9.10 ppm (H$_6$, pyridine, D, J=6 Hz)-1H at 8.80 ppm (NHCO, D, J=9 Hz)-1H at 8.35 ppm (H$_4$, pyridine, T, J=8 Hz)-1H at 8.22 ppm (H$_3$, pyridine, D, J=8 Hz)-1H at 7.94 ppm (H$_5$, pyridine, T, J=6 Hz)-1H at 7.00 ppm (H thiazole, S)-2H at 6.00 ppm (H$_7$ and —CH=, M)-5H between 5 and 5.5 ppm (H$_6$, CH$_2$N$^+$, CH$_2$=, M)-2H at 4.45 ppm (CH$_2$S, M)-2H at 4.0 ppm (CH$_2$→O, M).

EXAMPLE 3

Inner salt of 7-[2-(2-amino 4-thiazolyl) 2-(2-carboxy 2-propyl oxyimino)acetamido]3-(N-allyl 2-pyridinio thiomethyl)3-cepheme carboxylate S-oxide-1, syn isomer (CM 40 874 a)

To a solution of 0.3 g of CM 40 874 b obtained in Example 2 is added 0.7 g of ion exchanger resin Amberlite IRA 400 in the form of acetate and the mixture is stirred for 35 mins. at ambient temperature. The resin is filtered and washed with water. The solution is evaporated to dryness in vacuo at ambient temperature. The residue is taken up in 10 ml of ethanol and evaporated to dryness in vacuo at ordinary temperature. The residue is taken up in ether and the solid is drained. After drying, 0.210 g of the expected inner salt is obtained.

NMR spectrum: 1H at 8.5 ppm (NHCO, D, J=9 Hz)-1H at 8.0 ppm (H$_6$ pyridine, D, J=6 Hz)-1H at 7.45 ppm (H$_3$ pyridine, D, J=8 Hz)-1H at 7.30 ppm (H$_4$ pyridine, M)-2H at 7.25 ppm (NH$_2$; S.e.)-2H at 6.80 ppm (H thiazole, +H$_5$ pyridine, M)-2H at 6.00 ppm (H$_7$ and —CH=, M)-7H at 5.10 ppm (H$_6$, CH$_2$N$^+$,CH$_2$S—, CH$_2$=, M)-1H at 4.25 ppm (CH$_2$S→O, A of AB, J$_{AB}$=17 Hz)-1H at 3.80 ppm (CH$_2$S→O, B of AB=17 Hz)-6H at 1.45 ppm

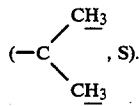

EXAMPLES 4 TO 9

Operation is as in Example 1 (c)—from the brominated derivative of Example 1 (b)—but varying the nature of the pyridine thione used.

By effecting thereafter the deprotection of the products thus obtained as indicated in Example 1 (d), the different compounds III shown in Table 1 are obtained.

In this Table, in addition to the structure and the characteristics of the products III obtained, the experimental conditions (temperature and duration) of the reaction of substitution of the brominated derivative by the thione which vary according to the reagents used, have also been indicated.

EXAMPLE 10

Trifluoroacetate of 7-[2-(2-amino 4-thiazolyl) 2-(1-carboxy 1-cyclobutyl oxyimino)acetamido]3-(N-allyl 2-pyridinio thiomethyl)3-cepheme 4-carboxylic S-oxide-1 acid, syn isomer (CM 40914)

(III) R$_1$+R$_2$=(CH$_2$)$_3$; R$_3$=CH$_2$=CH—CH$_2$; R$_4$=H; A=H; X$^-$=CF$_3$COO$^-$ (a) 7-[2-(2-tritylamino 4-thiazolyl) 2-(1-t-butoxycarbonyl 1-cyclobutyl oxyimino)acetamido]3-bromomethyl 3-cepheme carboxylate of 4-t-butyl S-oxide-1 syn isomer To a solution of 4.4 g of hydrochloride of 7-amino 3-bromomethyl 3-cepheme carboxylate of 4-t-butyl S-oxide-1 in 70 ml of anhydrous methylene chloride are added, in a nitrogen atmosphere, 1.5 ml of triethylamine, 5.1 g of 2-(2-tritylamino 4-thiazolyl) 2-(1-t-butoxycarbonyl 1-cyclobutyl oxyimino) acetic acid, syn isomer, 2.4 g of dicyclohexylcarbodiimide and 0.1 g of 1-hydroxy benzotriazole. The solution is stirred for 1 hour at ambient temperature then the dicyclohexylurea formed is filtered and the solution is concentrated to 20 ml in vacuo. It is chromatographed over a column of silica gel (150 g).

By elution with the hexane-ethyl acetate 40-60 (vol/vol) mixture, 4.8 g of the expected product are obtained after evaporation of the solvent.

NMR spectrum: 1H at 7.90 ppm (NHCO, D, J=9 Hz)-15H at 7.26 ppm (aromatic H, S)-1$\overline{\text{H}}$ at 6.97 ppm (NH-trityl, S.e.)-1H at 6.65 ppm (H thiazole, S)-1H at 6.1$\overline{8}$ ppm (H$_7$, D of D, J$_1$=9 Hz, J$_2$=4.5 Hz)-2H at 3.4 ppm (CH$_2$S→O, S.e.)-6H between 1.5 and 2.6 ppm (cyclobutyl, M)-9H at 1.45 ppm

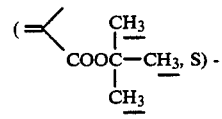

9H at 1.36 ppm

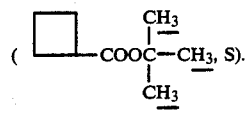

(b) Bromide of 7-[2-(2-tritylamino 4-thiazolyl)2-(1-t-butoxycarbonyl 1-cyclobutyl oxyimino)acetamido]3-(N-allyl 2-pyridinio thiomethyl) 3-cepheme carboxylate of t.butyl, syn isomer By using the brominated derivative of Example 9 (a) and by operating as in Example 1 (c), with N-allyl pyridine 2-thione, the expected compound is obtained in the form of a colourless solid.

(c) CM 40 914

From the above compound, deprotection is effected as indicated in Example 1 (d).

NMR spectrum 1H at 9.05 ppm (H$_6$ pyridine, D, J=6 Hz)-1H at 8.20 ppm (NH—CO, D, J=9 Hz)-3H between 7.6 and 8.5 ppm ($\overline{\text{H}}_3$, H$_4$, H$_5$ pyridine, M)-1H at 6.85 ppm (H thiazole, S)-2H at 6.0 ppm (H$_7$ and =CH, M)-5H between 4.8 and 5.5 ppm (H$_6$, CH$_2$=, CH$_2$N$^+$, M)-2H at 4.40 ppm (CH$_2$S, S.e.)-2H at 3.85 ppm (CH$_2$S→O, S.e.)-6H between 1.5 and 2.6 ppm ( , M).

EXAMPLES 11, 12, 13

Operation is as in Example 10 (b) from the brominated derivative of Example 10 (a) but varying the nature of the pyridine thione used.

By effecting deprotection thereafter as indicated in Example 1 (d), the compounds III shown in Table 2 are obtained.

EXAMPLE 14

Trifluoroacetate of 7-[2-(2-amino 4-thiazolyl)2-(1-carboxy 1-ethyl oxyimino)-acetamido]3-(2-N-methylpyridinio thiomethyl) 3-cepheme 4-carboxylic S-oxide-1 acid, syn isomer (CM 40 800)

(III) $R_1=H$; $R_2=CH_3$; $R_3=CH_3$; $R_4=H$; $A=H$; $X^-=CF_3COO^-$

Operation is as in Example 1, but replacing in step (b) the 2-(2-tritylamino 4-thiazolyl)2-(2-t-butoxycarbonyl 2-propyl oxyimino) acetic acid, syn isomer, by 2-(2-tritylamino 4-thiazolyl)2-(1-t-butoxycarbonyl 1-ethyl oxyimino) acetic acid, syn isomer.

Steps c and d are carried out identically and lead to the expected compound CM 40800.

NMR spectrum:
1H at 9.0 ppm (H$_6$ pyridine, M)-0.4H at 8.65 ppm (NHCO, D, J=9 Hz)-0.6H at 8.60 ppm (NHCO, D, J=9 Hz)-1H at 8.32 ppm (H$_4$ pyridine, M)-1H at 8.10 ppm (H$_3$ pyridine, D, J=6 Hz)-1H at 7.8 ppm (H$_5$ pyridine, M)-4H at 7.20 ppm (NH$_2$, 2 COOH, S.e.)-0.6H at 6.82 ppm (H thiazole, S)-0.4H at 6.80 ppm (H thiazole, S)-1H at 5.92 ppm (H$_7$, D of D, J$_1$=9 Hz, J$_2$=4 Hz)-1H at 5.0 ppm (H$_6$, M)-1H at 4.60 ppm

,

M)-1H at 4.50 ppm (CH$_2$S, D, J=12 Hz)-1H at 4.35 ppm (CH$_2$S, D, J=12 Hz)-3H at 4.20 ppm (CH$_3$N+—, S)-1H at 4.0 ppm (CH$_2$S→O, D, J=17 Hz)-1H at 3.87 ppm (CH$_2$S→O, D, J=17 Hz)-3H at 1.4 ppm

The division of the signals of the protons due to the —NH—CO group and to the thiazole indicates that CM 40 800 exists in the form of a mixture of 2 diastereoisomers due to the existence of an asymmetric carbon in the substituent of the oxime.

EXAMPLE 15

Trifluoroacetate of 7-[2-(2-amino 4-thiazolyl)2-(2-carboxy 2-propyl oxyimino)acetamido]3-(N-allyl 2-pyridinio thiomethyl) 3-cepheme 4-carboxylic S-oxide-1 acid, syn isomer (CM 40 874)

(a) Iodide of 3-(N-allyl 2-pyridinio thiomethyl) 7-formylamino 3-cepheme carboxylate of 4-potassium.

To the solution of 5.1 g of sodium iodide in 25 ml of water are added 17 g of the potassium salt of 7-formylamino cephalosporanic acid and 12.7 g of N-allyl-pyridine 2-thione.

The mixture is stirred for 4 hours at 60° C. After cooling, the solution is poured into 1.7 l of acetone and the precipitate is drained and rinsed with acetone then with ether. It is dried in vacuo.

(b) Chloride of 3-(N-allyl 2-pyridinio thiomethyl) 7-formylamino 3-cepheme 4-carboxylic acid.

20 g of the product obtained hereinabove are dissolved in 100 ml of water and the solution is acidified by 2N hydrochloric acid up to pH=1.5. The aqueous phase is separated from a slight precipitate and is poured over a column of ion exchanger resin Amberlite IRA 68® in the form of hydrochloride. It is eluted with water. The water is evaporated to dryness in vacuo and the residue is taken up in absolute ethanol. It is evaporated again to dryness and the residue is taken up in ether. The solid is drained and dried in vacuo.

NMR spectrum: 2H at 9.10 ppm (H$_6'$ pyridine, NHCO, M)-1H at 8.45 ppm (H$_4'$ pyridine, TD)-2H at 8.10 ppm (H—CO—N, H$_3'$ pyridine, M)-1H at 7.95 ppm (H$_5'$ pyridine, TD)-1H at 6.00 ppm (CH=, M)-1H at 5.70 ppm (H$_7$, M)-5H between 4.95 and 5.40 ppm (H$_6$, CH$_2$N⊕ and =CH$_2$, M)-2H at 4.45 ppm (CH$_2$S in 3, AB, J$_{AB}$=13 Hz) 2H at 3.60 ppm (CH$_2$S cycle, AB, J$_{AB}$=17 Hz).

(c) Chloride of 3-(N-allyl 2-pyridinio thiomethyl) 7-formylamino 3-cepheme 4-carboxylic S-oxide-1 acid.

6 g of the product obtained in (b) are dissolved in 30 ml of formic acid. 30 ml of methanol are added and the solution is cooled to 5° C. 2.7 g of metachloroperbenzoic acid are added in 5 minutes. The temperature is allowed to rise to 20° C. and the mixture is stirred at this temperature for 30 minutes.

An insoluble is filtered and the solution obtained is poured into 600 ml of ether. The solid is drained, rinsed with ether and dried in vacuo.

NMR spectrum: 1H at 8.96 ppm (H$_6'$ pyridine, D, J=6 Hz)-2H at 8.30 ppm (H$_4'$ pyridine, NH CO, M)-2H at 8.10 ppm (H$_3'$ pyridine, H—CO—N—, M)-1H at 7.80 ppm (H$_5'$ pyridine, TD, J=6 Hz)-1H at 6.0 ppm (CH=, M)-1H at 5.90 ppm (H$_7$, M)-5H between 5.0 and 5.50 ppm (CH$_2$ N⊕, CH$_2$=, H$_6$, M)-2H at 4.45 ppm (CH$_2$S, AB, J$_{AB}$=13 Hz)-2H at 3.95 ppm (CH$_2$S→O, AB, J$_{AB}$=17 Hz).

(d) Chloride of 3-(N-allyl 2-pyridinio thiomethyl) 7-formylamino 3-cepheme carboxylate of 4-diphenylmethyl S-oxide-1

4.5 g of the product obtained in (c) are dissolved in 45 ml of water and 130 ml of solution of diphenyldiazomethane in methylene chloride are added. The mixture is stirred vigorously and 90 ml of absolute ethanol are added and the pH is maintained at 2 by addition of concentrated hydrochloric acid.

After 45 minutes, the solution is decolored. The organic layer is decanted and the aqueous phase is reextracted with methylene chloride. The organic extracts are combined and concentrated to dryness. The residue is taken up in absolute ethanol and evaporated to dryness again. The residue is taken up in ether, the solid is drained and dried in vacuo.

NMR spectrum: 1H at 9.10 ppm (H$_6'$ pyridine, D, J=5 Hz)-1H at 8.45 ppm (CO NH, D, J=9 Hz) 1H at 8.20 ppm (H$_4'$ pyridine, T, J=7 Hz)-1H at 8.10 ppm (H CO—, S)-1H at 8.0 ppm (H$_3'$ pyridine, D, J=7 Hz)-1H at 7.85 ppm (H$_5'$ pyridine, deformed T)-10H at 7.30 ppm (aromatic H, M)-1H at 6.85 ppm (COO CH<,S)-2H at 6.00 ppm (H$_7$+CH=, M)-5H between 5 and 5.5 ppm (H$_6$, CH$_2$n⊕, =CH$_2$, M)-2H at 4.45 ppm (CH$_2$S, AB, J$_{AB}$=13 Hz) 2H At 4.0 ppm (CH$_2$→O, AB, J$_{AB}$=17 Hz).

(e) Hydrochloride of the chloride of 3-(N-allyl 2-pyridinio thiomethyl) 7-amino 3-cepheme carboxylate of diphenylmethyl, S-oxide-1

3 g of the product obtained hereinabove are dissolved in 10 ml of methanol in an inert atmosphere. The solution is cooled to 10° C. and 0.8 ml of thionyl chloride is added in 5 minutes, the temperature being maintained lower than 20° C.

The mixture is then stirred for 30 minutes at 20° C. and is poured into 300 ml of ether. The solid is drained and rinsed with ether. It is dried in vacuo over phosphoric anhydride.

(f) Chloride of 7-[2-(2-tritylamino 4-thiazolyl) 2-(2-t-butoxycarbonyl 2-propyl oxyimino)acetamido] 3-(N-allyl 2-pyridinio thiomethyl) 3-cepheme carboxylate of 4-diphenylmethyl S-oxide-1, syn isomer Chloride of 2-(2-tritylamino 4-thiazolyl) 2-(2-t-butoxycarbonyl 2-propyl oxyimino) acetic acid, syn isomer 3.4 g of 2-(2-tritylamino 4-thiazolyl) 2-(2-t-butoxycarbonyl 2-propyl oxyimino) acetic acid, syn isomer are suspended in an atmosphere of nitrogen in 20 ml of methylene chloride. 1.4 g of phosphorus pentachloride are added and the mixture is stirred for 30 minutes, the temperature being maintained lower than 0° C. The solution is poured into 200 ml of hexane. The solid is drained and dried in vacuo over phosphoric anhydride. The chloride of acid is used as such.

3.3 g of the derivative obtained in paragraph (e) are suspended in an atmosphere of nitrogen in 30 ml of methylene chloride. The mixture is cooled to 5° C. and 1.7 ml of dimethylaniline is added, then the chloride of acid obtained hereinabove, the temperature being allowed to rise to 20° C. After one hour of stirring, the solution is washed with 30 ml of a 0.5N hydrochloric acid solution. The organic solution is dried and the solvents are concentrated in vacuo up to a volume of 10–15 ml. This solution is poured into 150 ml of isopropyl ether. The solid is drained, rinsed with isopropyl ether and dried in vacuo.

The crude product thus obtained is chromatographed over a column of silica gel (120 g). By eluting with a methylene chloridemethanol 85-15 (vol/vol) mixture, the expected product is obtained.

NMR spectrum:
1H at 9.05 ppm ($H_6'$ pyridine, D, J=6 Hz)-1H at 8.85 ppm (NH Trit, s.e.)-2H at 8.25 ppm ($H_4'$ pyridine, NH CO, M)-1H at 8.0 ppm ($H_3'$ pyridine, D, J=7 Hz)-1H at 7.80 ppm ($H_5$, pyridine, TD)-25H at 7.27 ppm (aromatic H, M)-1H at 6.85 ppm (H thiazole, S)-1H at 6.75 ppm (COOC$\underline{H}$<, S)-2H at 5.95 ppm ($H_7$+C$\underline{H}$=, M)-5H between 5.0 and 5.5 ppm (C$\underline{H_2}N^{\oplus}$, C$\underline{H_2}$=, $H_6$, M)-2H at 4.45 ppm (C$\underline{H_2}$S, AB, $J_{AB}$=13 Hz)-2H at 4.0 ppm (C$\underline{H_2}$S—O, AB, $J_{AB}$=17 Hz)-6H at 1.40 ppm [(C$\underline{H_3}$)$_2$—C—, S]-9H at 1.30 ppm $$(-\underset{\underset{C\underline{H_3}}{|}}{\overset{\overset{C\underline{H_3}}{|}}{C}}-C\underline{H_3}, S).$$

(g) CM 40874

1 g of the protected product obtained in (f) is dissolved in 2 ml of anisole and cooled to 5° C. then 10 ml of trifluoroacetic acid are added. The temperature is allowed to rise to 20° C. and the mixture is left at this temperature for 2 hours.

The trifluoroacetic acid is evaporated in vacuo and the product is precipitated by addition of ether. The product is drained, washed with ether and dried.

NMR spectrum: 1H at 9.05 ppm ($H_6'$ pyridine, D, J=5 Hz)-1H at 8.50 ppm (NH CO, D, J=9 Hz)-1H at 8.35 ppm ($H_4'$ pyridine, M)-1H at 8.20 ppm ($H_3'$ pyridine, D, J=7 Hz)-1H at 7.95 ppm ($H_5'$ pyridine, M)-4H between 7 and 10 ppm (2 COO$\underline{H}$, N$\underline{H_2}$)-1H at 6.82 ppm (H thiazole, S)-2H at 6.0 ppm ($H_7$ and C$\underline{H}$=, M)-5H between 5.0 and 5.6 ppm (C$\underline{H_2}N^{\oplus}$, C$\underline{H_2}$= and $H_6$, M)-1H at 4.5 ppm (C$\underline{H_2}$S, A of AB, $J_{AB}$=13 Hz)-1 H at 4.32 ppm (C$\underline{H_2}$S, B of AB, $J_{AB}$=13 Hz)-1 H at 4.0 ppm (C$\underline{H_2}$S→O, A of AB, $J_{AB}$=17 Hz)-1 H at 3.8 ppm (C$\underline{H_2}$S→O, B of AB, $J_{AB}$32 17 Hz)-6 H at 1.45 ppm $$(-C\overset{\overset{CH_3}{\diagup}}{\underset{\underset{C\underline{H_3}}{\diagdown}}{}}, S).$$

This product is identical in all points with the product obtained in Example 1.

EXAMPLE 16

Trifluoroacetate of 7-[2-(2-amino 4-thiazolyl)-2(2-carboxy 2-propyl oxyimino)acetamido]-3-(N-allyl 2-pyridinio thiomethyl)3-cepheme 4-carboxylic S-oxide-1 acid, syn isomer (CM 40874)

(a) Iodide of 7-(5-phthalamino) 5-carboxy valeramido) 3-(N-allyl 2-pyridinio thiomethyl) 3-cepheme 4-carboxylic acid To the solution of 213 g of sodium iodide in 90 ml of water is added the mixture of 71 g of N-phthalyl cephalosporin C and 23.2 g of sodium bicarbonate. The mixture is heated to 60° C. and left with stirring for 1 hour 45 minutes at this temperature.

After cooling to 10° C., the mixture is poured into 5 liters of acetone with vigorous stirring. The solid is drained, rinsed with acetone and with ether.

The product is dried and disolved in 500 ml of water. The solution is cooled to 5° C.and acidified with stirring by the addition of 2N hydrochloric acid up to pH=2.5. The solid is drained, rinsed with a little iced water and dried in vacuo in the presence of phosphoric anhydride.

(b) Chloride, hydrochloride of 7-amino 3-(N-allyl-2-pyridinio thiomethyl) 3-cepheme-4-carboxylic acid 15 g of the product obtained in paragraph a) hereinabove are suspended, in an atmosphere of nitrogen, in 150 ml of methylene chloride, then 13 ml of dimethylaniline and 12 ml of chloro trimethylsilane are added. The temperature is raised to 32° C. and the solution is stirred at this temperature for 1 hour. The solution is cooled to −50° C. and 10 ml of dimethylaniline then 16 g of phosphorus pentachloride are added. The mixture is stirred at −50° C. for 1 hour then at −30° C. for 2 hours 30 minutes.

The mixture is poured onto a solution of 30 ml of 2,3-butanediol in 200 ml of methylene chloride cooled to −20° C. It is left with stirring until the temperature of the mixture has reached about 20° C. then the solid is drained. The mixture is washed with methylene chloride then with ether and is dried in vacuo over phosphoric anhydride.

NMR spectrum:
3H at 9.70 ppm (C$\underline{H_3}^+$, s.e.)-1H at 9.10 ppm ($H_6'$ pyridine, D, J=5 Hz)-1$\overline{H}$ at 8.50 ppm ($H_4'$ pyridine, D, J=7 Hz)-1H at 8.10 ppm ($H_3'$ pyridine, D, J=7Hz)-1H at 7.35 ppm ($H_5'$ pyridine, T)-1H at 6.05 ppm (C$\underline{H}$=, M)-6H between 5 and 5.5 ppm ($H_6$, $H_7$, C$\underline{H_2}\overline{N}^{\oplus}$, C$\underline{H_2}$=, M)-2H at 4.50 ppm (C$\underline{H_2}$S in 3, AB, $J_{AB}$=13 Hz)-2H at 3.80 ppm (C$\underline{H_2}$S cycle, S).

(c) Chloride, hydrochloride of 7-amino 3-(N-allyl 2-pyridinio thiomethyl) 3-cepheme 4-carboxylic S-oxide-1 acid 4 g of the product obtained hereinabove are dissolved in 15 ml of formic acid, then 20 ml of methanol are added.

The solution is cooled to 0° C. and 1.85 g of metachloroperbenzoic acid are added in 10 minutes. The solution is then stirred for 10 minutes at 10° C., then it is poured into 800 ml of ether. The precipitate is drained, washed with ether then dried in vacuo over phosphoric anhydride.

NMR spectrum:

1H at 9.05 ppm (H$_6$' pyridine, D, J=6 Hz)-1H at 8.40 ppm (H$_4$' pyridine, M)-1H at 8.10 ppm (H$_3$' pyridine, M)-1H at 7.90 ppm (H$_5$' pyridine, M)-1H at 6.00 ppm (=CH, M)-6H between 4.70 and 5.50 ppm (H$_6$, H$_7$, CH$_2$N$\oplus$, =CH$_2$M)-2H at 4.40 ppm (CH$_2$S, AB, J$_{AB}$=13 Hz)-2H at 3.90 ppm (CH$_2$S→O, AB, J$_{AB}$=17 Hz).

(d) Hydrochloride of the chloride of 3-N-allyl 2-pyridinio thiomethyl) 7-amino-3-cepheme 4-carboxylate of diphenylmethyl S-oxide-1

To the solution of 3.5 g of the product obtained in paragraph (c) in 30 ml of methanol are added 30 ml of a solution of diphenyl diazomethane, at 20° C. The solution is left for 30 minutes at this temperature then 40 ml of diphenyl diazomethane solution are added and the mixture is left for 1 hour at 20° C.

It is evaporated to dryness and taken up in a small quantity of methylene chloride and the solution is poured into ether. The solid is drained, rinsed with ether and dried in vacuo.

This product is identical to that obtained in Example 15(e).

(e) CM 40874

Using the above product, operation is as indicated in Example 15, paragraphs (f) and (g), to obtain the product CM 40874.

EXAMPLE 17

Hydrochloride, chloride of 7-[2-(2-amino 4-thiazolyl) 2-(2-carboxy 2-propyl oxyimino)acetamido] 3-(N-allyl 2-pyridinio thiomethyl) 3-cepheme 4-carboxylic S-oxide-1acid, syn isomer Operation is as in Example 15 up to paragraph (f) inclusive, then the protected compound thus obtained is treated with concentrated hydrochloric acid in formic acid as described in Example 2.

The compound is isolated in the same way.

Products (III) were studied as far as their pharmacological properties, and more especially their bacteriostatic action, are concerned.

In vitro bacteriostatic action were determined in a solid medium by the dilutions method. The results obtained are expressed in minimum inhibitory concentrations (MIC-μg/ml) and concern different strains of Enterobacteria and of Pseudomonas.

By way of comparison, the results obtained with 2 similar products described in the prior art have been added, namely: -7-[2-(2-amino thiazolyl) 2-carboxymethoxyimino acetamido]3-(2-pyridyl thiomethyl) 3-cepheme 4-carboxylic S-oxide-1 acid, syn isomer (compound A).

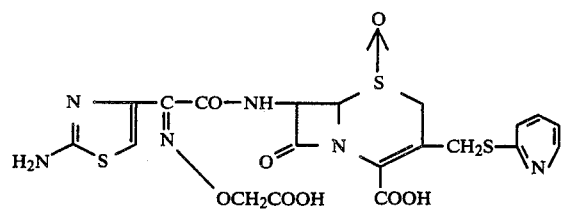

(Belgian Patent No. 886 038)

The trifluoroacetate of 7-[2-(2-amino 4-thiazolyl) 2-(2-carboxy 2-propyl oxyimino) acetamido]3-N-methyl 2-pyridinio thiomethyl) 3cepheme 4-carboxylic acid, syn isomer (compound B).

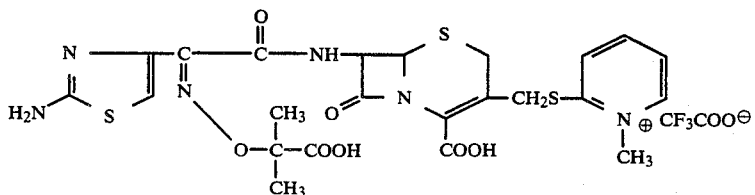

(German Patent Application No. 2 921 332)

The results obtained are shown in Table 3.

These results show a particularly interesting activity of the products according to the invention on strains which are usually hardly sensitive to the antibiotics of the cephalosporin family, namely the Enterobacteria and the Pseudomonas.

Compared with reference product A, products (III) show a surprizing activity on the following strains: Citrobacter, Enterobacter, Serratia and Pseudomonas, whilst conserving an activity at least equal to that of the reference product on Klebsiella and Proteus.

Compared with reference product B, products III show a clearly greater activity on Citrobacter, Proteus and Enterobacter, whilst conserving on the other strains an activity of the same order of magnitude and sometimes even greater.

Furthermore, the tests carried out on animals have demonstrated that there is no toxicity in the products according to the invention, their toxicity being comparable to that of the compounds of the cephalosporin family.

The products of the invention may therefore be used as antibiotics in human or veterinary medicine. They may be used in all sensitive-germ bacterial infections.

Pharmaceutical compositions are made from compounds (III) in their acid form or, when their solubility is insufficient, in the form of a salt.

The pharmaceutical compositions may be solid or liquid and be, for example, in the form of tablets, capsules, granules, ointments, creams, gels or injectable preparations.

Dosage may vary to considerable proportions, and depends in particular on the type and seriousness of the infection to be treated and on the mode of administration. In the adult by the injectable route, it is most often between 0.250 g and 4 g per day.

By way of example of a pharmaceutical composition containing a product of the invention, injectable ampoules containing:

CM 40 874 b: 1 g
Water for injectable preparation: 5 ml
Sodium carbonate q.s.p. pH=6.3
may be prepared.

TABLE 1

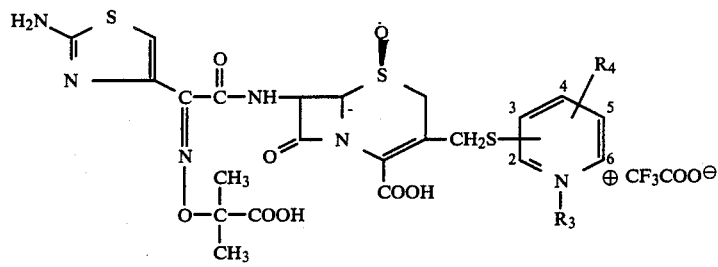

| Example No. | Code No. Product | R₃ | R₄ | Position substitution pyridine | Conditions temperature °C. - duration | NMR spectrum |
|---|---|---|---|---|---|---|
| 4 | 40763 | $CH_3$ | H | 2 | 20–24 hrs. | 1H at 9.00 ppm ($H_6$ pyridine, D, J = 6 Hz) - 4H between 7.60 and 8.60 ppm (N$\underline{H}$CO, $H_3$, $H_4$, $H_5$ pyridine, M) - 1H at 6.83 ppm (H thiazole, S) - 1H at 5.97 ppm ($H_7$, M) - 1H at 5.00 ppm ($H_6$, D, J = 4 Hz) - 2H at 4.40 ppm ($C\underline{H}_2$S, S.e.) - 3H at 4.20 ppm ($C\underline{H}_3$—$N^+$, S) - 2H at 3.80 ppm ($C\underline{H}_2$S→O, S.e.) - 6H at 1.46 ppm (—C(CH₃)(CH₃), S). |
| 5 | 40876 | $CH_3$ | H | 4 | 20–3 hrs. | 2H at 8.64 ppm ($H_2$, $H_6$ pyridine, D, J = 7 Hz) - 1H at 8.40 ppm (N$\underline{H}$ CO, D, J = 9 Hz) - 2H at 7.95 ppm ($H_3$, $H_5$ pyridine, D, J = 7 Hz) - 4H at 7.50 ppm ($NH_2$, 2 COO$\underline{H}$, S.e.) - 1H at 6.80 ppm (H thiazole, S) - 1H at 5.95 ppm ($H_7$, D of D, $J_1$ = 9 Hz, $J_2$ = 4 Hz) - 1H at 5.05 ppm ($H_6$, D, J = 4 Hz) - 1H at 4.40 ppm ($C\underline{H}_2$S, A of AB, $J_{AB}$ = 13 Hz) - 1H at 4.35 ppm ($C\underline{H}_2$S, B of AB $J_{AB}$ = 13 Hz) - 3H at 4.16 ppm ($C\underline{H}_3N^+$, S) - 1H at 3.89 ppm ($C\underline{H}_2$S→O, A of AB, $J_{AB}$ = 17 Hz) - 1H at 3.76 ppm ($C\underline{H}_2$S→O, B of AB, $J_{AB}$ = 17 Hz) - 6H at 1.43 ppm (—C(CH₃)(CH₃), 2 D). |
| 6 | 40912 | $CH_2C\equiv CH$ | H | 2 | 20–4 hrs. | 5H from 7.5 to 9.1 ppm ($H_3$, $H_4$, $H_5$ and $H_6$ pyridine and N$\underline{H}$CO, M) - 1H at 6.85 ppm (H thiazole, S) - 1H at 6.0 ppm ($H_7$, M) - 2H at 5.65 ppm ($C\underline{H}_2N^+$, M) - 3H at 5.0 ppm ($H_6$ and $C\underline{H}_2$S, M) - 2H at 3.95 ppm ($C\underline{H}_2$S→O, S.e.) - 6H at 1.43 ppm (—C(CH₃)(CH₃), S) - [≡C$\underline{H}$ masked by the dimethylsulfoxide] |
| 7 | 40972 | $CH_3$ | 3-OH | 2 | 20–24 hrs. | 5H between 6.5 and 10 ppm ($H_2N$, 2 COO$\underline{H}$, O$\underline{H}$, M) - |

TABLE 1-continued

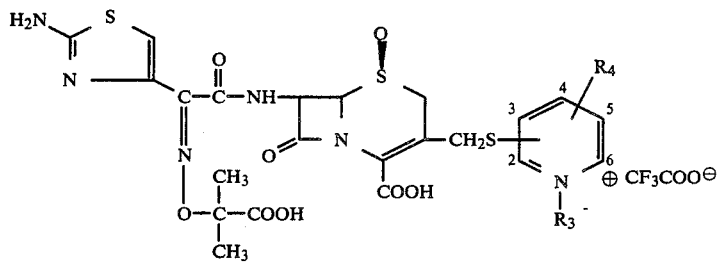

| Example No. | Code No. Product | R₃ | R₄ | Position substitution pyridine | Conditions temperature °C. - duration | NMR spectrum |
|---|---|---|---|---|---|---|
| | | | | | | 1H at 8.60 ppm (H₆ pyridine, M) - 1H at 8.45 ppm (N$\underline{H}$CO, D, J = 9 Hz) - 2H at 7.9 ppm (H₄ and H₅ pyridine, M) - 1H at 6.80 ppm (H thiazole, S) - 1H at 6.0 ppm (H₇, M) - 1H at 4.96 ppm (H₆, D, J = 5 Hz) - 5H at 4.30 ppm (C$\underline{H_3}$N⁺ and C$\underline{H_2}$S, M) - 2H at 3.85 ppm (C$\underline{H_2}$S→O, M) - 6H at 1.47 ppm $(-C\!\!\begin{array}{c}\underline{CH_3}\\ \underline{CH_3}\end{array}, S)$. |
| 8 | 41087 | CH₂COOC₂H₅ | H | 2 | 5–16 hrs. solvent tetrahydrofuran | 1H at 9.2 ppm (N$\underline{H}$CO, D, J = 9 Hz) - 4H between 7.5 and 8.8 ppm (H₃, H₄, H₅ and H₆ pyridine, M) - 1H at 6.90 ppm (H thiazole, S) - 1H at 6.0 ppm (H₇, M) - 2H at 5.67 ppm (C$\underline{H_2}$N⁺, S.e.) - 1H at 5.0 ppm (H₆, D, J = 5 Hz) - 2H at 4.30 ppm (COOC$\underline{H_2}$—, Q, J = 7 Hz) - 2H at 3.90 ppm (C$\underline{H_2}$S→O, S.e.) - 6H at 1.45 ppm $(-C\!\!\begin{array}{c}\underline{CH_3}\\ \underline{CH_3}\end{array}, S)$ - 3H at 1.20 ppm (COOCH₂C$\underline{H_3}$, T, J = 7 Hz). |
| 9 | 41607 | —CH₂—CH=CH₂ | H | 4 | 20° C. 2 hours | 2H at 8.70 ppm (Hα pyridine, D, J = 6 Hz) - 1H at 8.45 ppm (N$\underline{H}$—CO, D, J = 9 Hz) - 2H at 8.0 ppm (Hβ pyridine, D, J = 6 Hz) - 1H at 6.80 ppm (H thiazole, S) - 2H at 6.0 ppm (H₇ + C$\underline{H}$=, M) - 2H at 5.40 ppm (=C$\underline{H_2}$, M) - 3H at 5.05 ppm (H₆ + C$\underline{H_2}$N⊕, M) - 2H at 4.45 ppm (C$\underline{H_2}$S, M) - 2H at 3.80 ppm (C$\underline{H_2}$S→O, AB, J$_{AB}$ = 16 Hz) - 6H at 1.45 ppm (C—(CH₃)₂, 2 S). |

TABLE 2

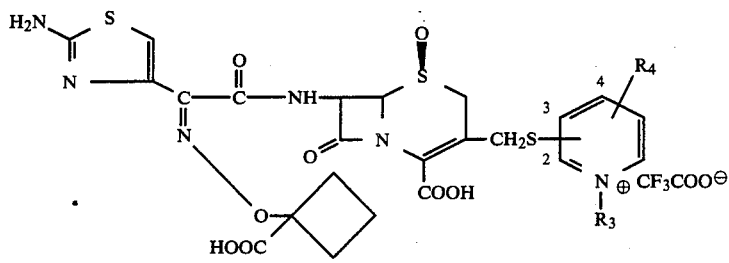

| Example No. | Code No. product | R₃ | R₄ | Position substitution pyridine | Conditions temperature °C. - duration | NMR spectrum |
|---|---|---|---|---|---|---|
| 11 | 40882 | $CH_3$ | H | 2 | 20-5 hrs. | 9H between 7.5 and 9.5 ppm ($NH_2$, 2 COO$\underline{H}$, N$\underline{H}$CO, $H_3$, $H_4$, $H_5$ and $H_6$ pyridine, M) - 1H at 6.88 ppm (H thiazole, S) - 1H at 6.0 ppm ($H_7$, M) - 1H at 5.07 ppm ($H_6$, D, J = 4 Hz) - 2H at 4.45 ppm (C$\underline{H_2}$S—M) - 3H at 4.25 ppm (C$\underline{H_3}$N⁺, S) - 2H at 3.93 ppm (C$\underline{H_2}$S→O, M) - 6H between 1.5 and 2.7 ppm ⬦, M). |
| 12 | 40954 | $CH_3$ | H | 4 | 20-16 hrs. | 7H between 8.3 and 9.0 ppm (N$\underline{H}$CO, $NH_2$, 2 COO$\underline{H}$, $H_2$ and $H_6$ pyridine, M) - 2H at 7.90 ppm ($H_3$ and $H_5$ pyridine, D, J = 6 Hz) - 1H at 6.82 ppm (H thiazole, S) - 1H at 6.00 ppm ($H_7$, D of D, $J_1$ = 9 Hz, $J_2$ = 5 Hz) - 1H at 5.0 ppm ($H_6$, D, J = 5 Hz) - 2H at 4.40 ppm (C$\underline{H_2}$S, S.e.) - 3H at 4.20 ppm (C$\underline{H_3}$—N⁺, S) - 2H at 3.80 ppm (C$\underline{H_2}$S→O, S.e.) - 6H between 1.5 and 3 ppm (⬦, M). |
| 13 | 41647 | $-CH_2-CH=CH_2$ | H | 4 | 20° C. 1 hour | 1H at 8.80 ppm (N$\underline{H}$—CO, D, J = 9 Hz) 2H at 8.70 ppm (Hαpyridine, D, J = 6 Hz) - 2H at 8.0 ppm (Hβpyridine, D, J = 6 Hz) - 1H at 6.80 ppm (H thiazole, S) - 2H at 6.00 ppm $H_7$ + C$\underline{H}$=, M) - 2H at 5.40 ppm C$\underline{H_2}$=, M) - 3H at 5.05 ppm ($H_6$ + C$\underline{H_2}$N⊕,M) - 2H at 4.45 ppm (C$\underline{H_2}$S, M) - 2H at 3.8 ppm (C$\underline{H_2}$S→O, AB, $J_{AB}$ = 16 Hz) - 4H at 2.45 ppm (CH₂—C(COOH)—CH₂, M) - 2H at 1.9 ppm (CH₂—CH₂). |

TABLE 3

| Strain | \multicolumn{10}{c}{Product} |
|---|---|---|---|---|---|---|---|---|---|---|
| | 40874 | 40914 | 40763 | 40876 | 40800 | 40882 | 40954 | 41087 | A | B |
| Citrobacter 49 | 4 | 4 | 2 | 1 | 2 | 4 | 2 | 0.5 | 16 | 8 |
| Proteus 150 | 0.031 | ≦0.125 | ≦0.125 | ≦0.125 | 0.25 | ≦0.125 | ≦0.125 | 0.25 | 0.25 | 4 |
| Serratia RL 72 | 0.5 | 0.25 | 0.25 | 0.25 | 2 | 0.25 | 0.25 | 2 | 32 | 2 |
| Klebsiella RO 30 | 0.25 | ≦0.125 | 0.25 | ≦0.125 | 0.25 | ≦0.125 | ≦0.125 | 0.5 | 0.5 | 0.25 |
| Enterobacter RO 46 | 0.5 | 0.25 | 0.5 | 0.25 | 0.25 | 0.25 | ≦0.125 | 1 | 8 | 64 |
| Enterobacter P 99 | 0.5 | 0.5 | 1 | 0.5 | 1 | 0.5 | 0.5 | 2 | 16 | 256 |
| Pseudomonas A 22 IP | 8 | 8 | 4 | 2 | 16 | 2 | 2 | — | >256 | 8 |
| Pseudomonas RL 112 | 8 | 8 | 4 | 4 | 8 | 4 | 4 | — | 256 | 16 |

What is claimed is:

1. Cephalosporins having the formula:

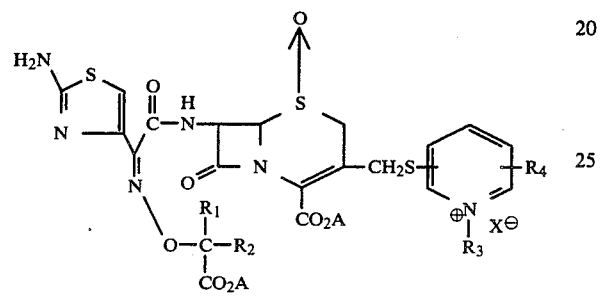

wherein
$R_1$ is H or $CH_3$; $R_2$ is $CH_3$; or $R_1$ and $R_2$ taken together constitute a 1,3-propylene group;
$R_3$ is an alkyl, alkenyl, or alkynyl group of from one to four carbons; or a $CH_2COOAlk$ group wherein Alk is alkyl of from one to four carbons;
$R_4$ denotes or OH occupying a free position on the pyridine ring; the atom of sulfur of the thiomethyl group being bonded to the 2 or 4 position of the pyridine;
A is selected from the group consisting of hydrogen;
alkali metal cations;
alkaline earth cations;
cations, resulting from protonation of a compound selected from the group consisting of ethylenediamine, ethanolamine, and tromethamine;
tertiary butyl;
organic radicals selected from the group consisting of phthalidyl; pivaloyloxymethyl, acetoxymethyl, ethoxycarbonyloxymethyl, 1-(ethoxycarbonyloxy) ethyl, acetonyl, α-methoxy α-carbomethoxymethyl, carbomethoxymethyl, and carbethoxymethyl;
$X^\ominus$ represents an anion selected from the group consisting of chloride, bromide, acetate, trifluoroacetate, formate, and the carboxylate anion derived from the carboxyl group located on the 4-position of the cepheme ring system; or a pharmaceutically acceptable acid addition salt of the compound in which A is H, tertiary butyl, or said organic radical.

2. A cephalosporin in the syn isomer form having its formula:

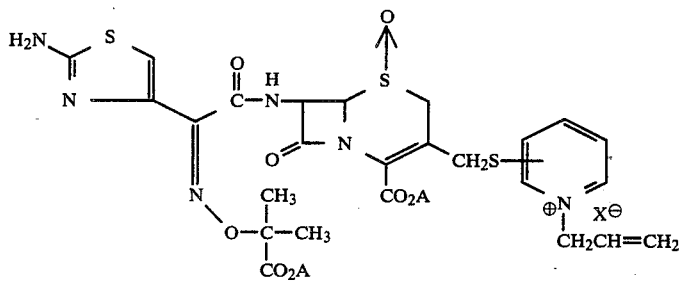

wherein
A is selected from the group consisting of hydrogen; alkali metal cations;
alkaline earth cations;
cations resulting from protonation of a compound selected from the group consisting of ethylenediamine, ethanolamine, and tromethamine;
tertiary butyl;
organic radicals selected from the group consisting of phthalidyl, pivaloyloxymethyl, acetoxymethyl, ethoxycarbonyloxymethyl, 1-(ethoxycarbonyloxy)ethyl, acetonyl, α-methoxy αcarbomethoxymethyl, carbomethoxymethyl, and carbethoxymethyl;
$X^-$ represents an anion selected from the group consisting of chloride, bromide, acetate, trifluoroacetate, and formate;
or a pharmaceutically acceptable acid addition salt of the compound in which A is H, tertiary butyl, or said organic radical.

3. A cephalosporin inner quaternary salt in the syn isomer form having the formula

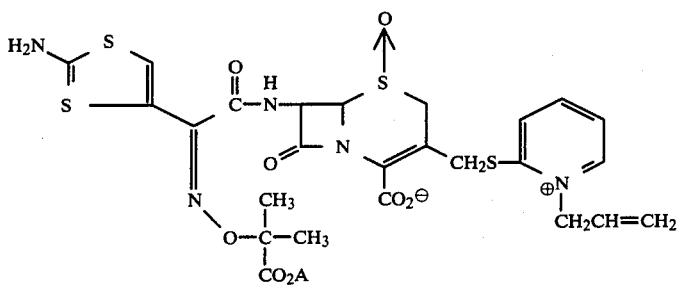

wherein
A is selected from the group consisting of hydrogen; alkali metal cations;
alkaline earth cations;
cations resulting from protonation of a compound selected from the group consisting of ethylenediamine, ethanolamine and tromethamine;
tertiary butyl;
organic radicals selected from the group consisting of phthalidyl, pivaloyloxymethyl, acetoxymethyl, ethoxycarbonyloxymethyl, 1-(ethoxycarbonyloxy) ethyl, acetonyl, α-methoxy α-carbomethoxymethyl, carbomethoxymethyl, and carbethoxymethyl;
or a pharmaceutically-acceptable acid addition salt of the compound in which A is H, tertiary butyl, said organic radical.

4. A cephalosporin according to claim 1, selected from the group consisting of the trifluoroacetate, the bromide of the hydrochloride and the chloride of the hydrochloride of 7-[2-(2-amino 4-thiazolyl)2-(2-carboxy 2-propyloxyimino)acetamido]3(N-allyl 2-pyridinio thiomethyl)3-cepheme 4-carboxylic S-oxide-1 acid.

5. An antiobiotic pharmaceutical composition comprising a pharmaceutically effective amount of a cephalosporin of claim 1 plus a pharmaceutically acceptable carrier.

6. An antibiotic pharmaceutical composition comprising a pharmaceutically effective amount of a cephalosporin of claim 2 plus a pharmaceutically acceptable carrier.

7. An antibiotic pharmaceutical composition comprising a pharmaceutically effective amount of a cephalosporin of claim 3 plus a pharmaceutically acceptable carrier.

8. A cephalosporin having the formula

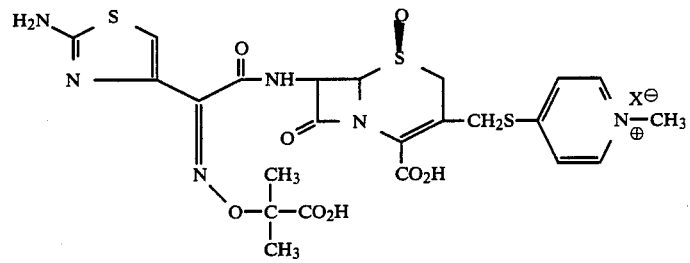

wherein $X^{(-)}$ is an anion selected from the group consisting of chloride, bromide, acetate, trifluoroacetate, formate, and the carboxylate anion derived from the carboxyl group located on the 4-position of the cepheme ring system; or a pharmaceutically-acceptable acid addition salt thereof.

9. The cephalosporin of claim 8 wherein the $X^{(-)}$ anino is trifluoroacetate.

10. An antibiotic pharmacuetical composition comprising a pharmaceutically effective amount of a cephalosporin of claim 8 plus a pharmaceutically-acceptable carrier.

11. An antibiotic pharmaceutical composition comprising a pharmaceutically effective amount of the cephalosporin of claim 9 plus a pharmaceutically-acceptable carrier.

* * * * *

UNITED STATES PATENT AND TRADEMARK OFFICE
CERTIFICATE OF CORRECTION

PATENT NO. : 4,593,022
DATED : June 3, 1986
INVENTOR(S) : Bernard Labeeuw and Ali Salhi It is certified that error appears in the above—identified patent and that said Letters Patent is hereby corrected as shown below:

Column 2, line 65, "quaternay" should read -- quarternary --

Column 3, line 18, "salt." should read -- salt; --

Column 4, line 7, 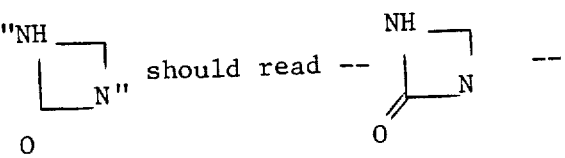

line 19, "7-[2(2" should read -- 7-[2-(2 --

Column 5, line 23, "to" should read -- To -- line 31, "50°C." should read -- 50°C -- line 48, "50°C." should read -- 50°C --

Column 8, line 5, 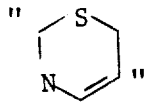

Column 9, line 34, "ester)" should read -- ester -- line 49, "Compounds XIII" should read -- Compounds XII --

UNITED STATES PATENT AND TRADEMARK OFFICE
CERTIFICATE OF CORRECTION

PATENT NO. : 4,593,022

DATED : June 3, 1986

INVENTOR(S) : Bernard Labeeuw and Ali Salhi

It is certified that error appears in the above—identified patent and that said Letters Patent is hereby corrected as shown below:

Column 11, line 30, "S-oxide 1," should read -- S-oxide-1, -- line 57, "$(-\overset{|}{\underset{|}{C}}-CH_3, S)-$" should read -- $(-\overset{|}{\underset{|}{C}}-\underline{CH_3}, S)$ -- line 64, "$(-\overset{|}{\underset{|}{C}}-, S)-$" should read -- $(-\overset{|}{\underset{|}{C}}-, S)$ --

Column 12, line 8, "(c)" should read -- c) --
line 31, "ppl" should read -- ppm --
line 34, "ppl" should read -- ppm --

Column 14, line 53, "spectrum 1H" should read -- spectrum:-1H --
line 59, "(   ," should read -- $(\diamondsuit<$ ,--

Column 15, line 27, "$\underset{'CH,}{CH}$" should read -- $\left(\underset{'CH,M}{CH}\right)$ --
line 30, "M)-1H" should read -- -1H --
line 30, "CH$_2$S" should read -- "$\underline{CH_2}$ S -- line 68, "68 R" should read -- 68 ® --

Column 16, line 35, "S-oxide-1" should read -- S-oxide-1. --
line 61, "S-oxide-1" should read -- S-oxide-1. --

Column 17, line 6, "isomer" should read -- isomer. --
line 10, "isomer" should read -- isomer. --

Column 18, line 4, "$J_{AB}$ 32 17Hz)-6H" should read -- $J_{AB} = 17Hz$) -6H -- line 8, "$(-C\overset{CH_3}{\underset{CH_3}{<}},S).$" should read -- $(-\overset{CH_3}{\underset{CH_3}{C-}},S).$ -- line 39, "acid" should read -- acid. --

UNITED STATES PATENT AND TRADEMARK OFFICE
CERTIFICATE OF CORRECTION

PATENT NO. : 4,593,022

DATED : June 3, 1986

INVENTOR(S) : Bernard Labeeuw and Ali Salhi

It is certified that error appears in the above—identified patent and that said Letters Patent is hereby corrected as shown below:

Column 19, line 18, "3-N-allyl" should read -- 3-(N-allyl --
        line 53, "isomer" should read -- isomer. --
        line 62, "were" should read -- was --

Column 20, line 44, "III" should read -- (III) --

Column 22, line 32, "(-C(CH$_3$)(CH$_3$), S)" should read -- (-C-(CH$_3$)(CH$_3$), S) -- line 56, "(-C(CH$_3$)(CH$_3$), 2D)" should read -- (-C-(CH$_3$)(CH$_3$), 2D) --

Column 24, line 19, "pyridine." should read -- pyridine, -- line 27, "(-C(CH$_3$)(CH$_3$), S)" should read -- (-C-(CH$_3$)(CH$_3$), S) -- line 44, "(-C(CH$_3$)(CH$_3$), S)" should read -- (-C-(CH$_3$)(CH$_3$), S) -- line 53, "(=CH$_2$), M)-" should read -- =CH$_2$, M) --

Column 26, line 22, "(CH$_2$ S-M)-" should read -- (CH$_2$ S,M) --

UNITED STATES PATENT AND TRADEMARK OFFICE
CERTIFICATE OF CORRECTION

PATENT NO. : 4,593,022

DATED : June 3, 1986

INVENTOR(S) : Bernard Labeeuw and Ali Salhi

It is certified that error appears in the above—identified patent and that said Letters Patent is hereby corrected as shown below:

Column 27, line 7, "Proteus 150" should read -- Proteus 1510 --
line 67, "phthalidyl;" should read -- phthalidyl, --

Column 28, line 28, "isomer" should read -- isomeric --
line 28, "its" should read -- the --
line 58, "a-carbomethox-" should read -- α-carbomethox- --
line 68, "isomer" should read -- isomeric --

Column 30, line 44, "anino" should read -- anion --

Signed and Sealed this

Fifteenth Day of March, 1988

Attest:

DONALD J. QUIGG

Attesting Officer

Commissioner of Patents and Trademarks